US009018584B2

(12) United States Patent
Chernokalskaya et al.

(10) Patent No.: US 9,018,584 B2
(45) Date of Patent: Apr. 28, 2015

(54) DEVICES AND METHODS FOR INFRARED (IR) BASED QUANTITATION OF BIOMOLECULES

(75) Inventors: Elena Chernokalskaya, Lexington, MA (US); Vivek Joshi, Chelmsford, MA (US); Phillip Clark, Wakefield, MA (US); Christopher Utzat, Andover, MA (US); Ryan Amara, Tewksbury, MA (US); Timothy Scott Rider, Exeter, NH (US)

(73) Assignee: EMD Millipore Corporation, Billerica, MA (US)

( * ) Notice: Subject to any disclaimer, the term of this patent is extended or adjusted under 35 U.S.C. 154(b) by 260 days.

(21) Appl. No.: 13/415,400

(22) Filed: Mar. 8, 2012

(65) Prior Publication Data
US 2013/0062523 A1  Mar. 14, 2013

Related U.S. Application Data

(60) Provisional application No. 61/475,434, filed on Apr. 14, 2011.

(51) Int. Cl.
*G01N 21/25* (2006.01)
*G01N 21/3563* (2014.01)
*G01J 5/02* (2006.01)
*G01N 21/3577* (2014.01)
*G01N 21/359* (2014.01)

(52) U.S. Cl.
CPC ............ *G01N 21/25* (2013.01); *G01N 21/3563* (2013.01); *G01N 2021/3572* (2013.01); *G01J 5/0255* (2013.01); *G01N 21/3577* (2013.01); *G01N 21/359* (2013.01)

(58) Field of Classification Search
CPC .................................. G01N 21/25; G01J 5/02
USPC ................................... 250/339.07; 73/864.91
See application file for complete search history.

(56) References Cited

U.S. PATENT DOCUMENTS

| | | | |
|---|---|---|---|
| 4,618,475 A | 10/1986 | Wang | |
| 4,734,112 A | 3/1988 | Okita et al. | |
| 5,470,757 A | 11/1995 | Gagnon et al. | |
| 5,605,838 A | 2/1997 | Backhaus et al. | |
| 5,764,355 A * | 6/1998 | Gagnon et al. | 356/244 |
| 5,766,473 A | 6/1998 | Strobel et al. | |
| 5,786,226 A | 7/1998 | Bocker et al. | |

(Continued)

FOREIGN PATENT DOCUMENTS

| | | |
|---|---|---|
| CN | 1549921 A | 11/2004 |
| CN | 1815189 A | 8/2006 |

(Continued)

OTHER PUBLICATIONS

Extended European Search Report (includes Supplementary European Search Report and Search Opinion) received for European Patent Application No. 12162822.6, mailed on Oct. 8, 2013, 12 pages.
Carrilho et al., "Paper Microzone Plates", Analytical Chemistry, vol. 81, No. 15, Aug. 1, 2009, pp. 5990-5998.
International Search Report and Written Opinion received for PCT Patent Application No. PCT/US2012/028273, mailed on May 24, 2012, 9 pages.

(Continued)

*Primary Examiner* — David Porta
*Assistant Examiner* — Faye Boosalis
(74) *Attorney, Agent, or Firm* — EMD Millipore Corporation

(57) ABSTRACT

The present invention provides methods for quantitating one or more biomolecules in a sample using IR based techniques, sample holder devices for use in such methods as well as methods for manufacturing such sample holder devices.

24 Claims, 18 Drawing Sheets

(56) References Cited

U.S. PATENT DOCUMENTS

| | | |
|---|---|---|
| 5,958,345 A | 9/1999 | Turner et al. |
| 6,287,872 B1 | 9/2001 | Schurenberg et al. |
| 6,983,177 B2 | 1/2006 | Rule et al. |
| 7,547,556 B2 | 6/2009 | Hunter et al. |
| 8,263,360 B2 | 9/2012 | Mossoba et al. |
| 8,546,752 B2 * | 10/2013 | Henion et al. ............... 250/288 |
| 2002/0127589 A1 | 9/2002 | Sato et al. |
| 2008/0311616 A1 | 12/2008 | Mossoba et al. |
| 2009/0075837 A1 | 3/2009 | Burke et al. |
| 2012/0152041 A1 * | 6/2012 | Maier ...................... 73/864.91 |

FOREIGN PATENT DOCUMENTS

| | | |
|---|---|---|
| JP | 7-167779 A | 7/1995 |
| JP | 2001-511882 A | 8/2001 |
| JP | 2010-8290 A | 1/2010 |
| WO | 97/25608 A1 | 7/1997 |
| WO | 2006/011487 A1 | 2/2006 |
| WO | 2009/058867 A2 | 5/2009 |

OTHER PUBLICATIONS

International Preliminary Report on Patentability received for PCT Patent Application No. PCT/US2012/028273, mailed on Oct. 24, 2013, 5 pages.

FT-IR Instrument, "ALPHA FT-IR Spectrometer", Instrument Overview online available at <http://www.brukeroptics.com/alpha.html?&L=0&print=1%253f>, retrieved on Mar. 20, 2011, 2 pages.

Kerslake et al., "Pharmaceutical and Biomedical Applications of Fiber Optic Biosensors Based on Infra Red Technology", Advanced Drug Delivery Reviews, vol. 21, 1996, pp. 205-213.

Loebke et al., "Infrared-Based Protein Detection Arrays for Quantitative Proteomics", Proteomics, vol. 7, 2007, pp. 558-564.

Sakai et al., "Quantitative and Non-Destructive Analyses of Fatty Acid Esters and Cholesterol in Brain Tissues by Fourier Transform Infrared Spectroscopy", Vibrational Spectroscopy, vol. 7, 1994, pp. 163-167.

* cited by examiner

DEVICES AND METHODS FOR INFRARED (IR) BASED QUANTITATION OF BIOMOLECULES

CROSS-REFERENCE TO RELATED APPLICATIONS

This application claims the benefit of priority of U.S. Provisional Patent Application No. 61/475,434, filed on Apr. 14, 2011, the entire content of which is incorporated by reference herein in its entirety.

FIELD OF INVENTION

This invention relates to the field of infrared spectrophotometric methods for quantitation of analytes in a sample and devices for use in the methods.

BACKGROUND

Infrared (IR) spectroscopy is a commonly used analytical tool in research laboratories for analysis of samples. The IR region of the electromagnetic spectrum extends from the lower end of the visible region (wavenumber of approximately 14,300 $cm^{-1}$) to the microwave region (near 20 $cm^{-1}$). Usually, for a molecule to absorb IR, the vibrations or rotations within the molecule must cause a net change in the dipole moment of the molecule. The alternating electrical field of the radiation interacts with fluctuations in the dipole moment of the molecule and if the frequency of the radiation matches the vibrational frequency of the molecule, then the radiation is absorbed, thereby causing a-change in the amplitude of the molecular vibration.

Typically, for the quantitative analysis of biomolecules, e.g., proteins, the most commonly used techniques are colorimetric techniques (e.g., the Coomassie blue assay, the Lowry assay, the BCA assay and the Pierce 660 Protein assay) and UV spectroscopic techniques (e.g., absorption at 280 nm). In case of most quantitation methods known in the art, a user needs to generate a calibration curve using a calibrant which typically is the same molecule as the analyte being quantitated, each time a user carries out the quantitation.

SUMMARY OF THE INVENTION

The present invention provides improved methods for quantitation of analytes, especially biomolecules, in a sample, which require less time to perform as well as less sample volume than most methods known in the art and, further, do not require any special sample preparation steps, as do most methods known in the art. Further, the methods according to the present invention also obviate the need for a user to generate a calibration curve each time an analyte is quantitated and also do not require that the calibrant be the same molecule as the analyte being quantitated. The present invention also provides devices for use in the claimed methods.

In one aspect according to the present invention, an IR based method for quantitating one or more biomolecules in a sample is provided.

In one method for quantitation of one or more biomolecules in a sample according to the present invention, the method comprises the steps of: (a) providing a sample holder comprising a porous membrane which comprises a hydrophilic region surrounded by a hydrophobic region for sample containment; (b) contacting the hydrophilic region of the membrane with a sample volume; (c) drying the sample volume on the membrane; (d) exposing the sample volume on the membrane to an infrared beam comprising a wavelength in the spectral range of 4000-400 $cm^{-1}$, or any portion of the spectral range, thereby to obtain an infrared absorption spectrum; where one or more absorption peak areas in the infrared absorption spectrum correlates with the quantity of the one or more biomolecules in the sample.

In another method for quantitation of one or more biomolecules in a sample according to the present invention, the method comprises the steps of: (a) providing a sample holder comprising a porous membrane which comprises a hydrophilic region surrounded by a hydrophobic region for sample containment; (b) contacting the hydrophilic region of the membrane with a sample volume; (c) drying the sample volume on the membrane; (d) detecting the presence of water in the sample volume after step (c) by infrared absorbance and repeating step (c), if necessary, until presence of water is undetectable; and (e) exposing the dried sample volume on the membrane to an infrared beam comprising a wavelength in the spectral range of 4000-400 $cm^{-1}$ or any portion of the spectral range, thereby to obtain an infrared absorption spectrum; where one or more absorption peak areas in the infrared absorption spectrum correlates with the quantity of the one or more biomolecules in the sample.

In some embodiments according to the claimed methods, the one or more biomolecules is selected from the group consisting of nucleic acids, proteins, lipids, polysaccharides, and lipopolysaccharides. An exemplary lipopolysaccharide is an endotoxin.

In various embodiments, each of the one or more absorption peak areas in the spectrum correlates with the quantity of a particular biomolecule in the sample.

In some embodiments, a method according to the claimed invention does not require the generation of a calibration curve each time an analyte is quantitated.

In some embodiments according to the present invention, one or more calibration curves are pre-loaded onto the instrument used, thereby obviating the need to generate a calibration curve each time a user wishes to quantitale an analyte in a sample. In the case of protein and peptide quantitation, the quantitation is based on the number of amide bonds or the concentration of amide bonds present in the polypeptide molecule and, accordingly, the quantitation is independent of the amino acid sequence of the molecule. Consequently, unlike most methods known and used in the art which require the generation of a calibration curve each time an analyte (e.g., protein or peptide) is quantitated and further require that the calibrant be the same molecule as the analyte being quantitated, in the methods according to the claimed invention, any protein may be used as a calibrant for the generation of a calibration curve which is subsequently pre-loaded onto the instrument being used.

Similarly, in case of other analytes, e.g., nucleic acids, carbohydrates etc., any suitable calibrant may be used for the generation of a calibration curve which is pre-loaded onto an instrument being used. The methods according to the present invention can be used for quantitating analytes in a very small sample volume. In various embodiments according to the claimed methods, the sample volume ranges from 0.1 to 20 µl. In a particular embodiment, the sample volume is about 2 to 5 µl or less, or less than 1 µl.

In some embodiments, the sample comprises a biological fluid such as, for example, blood, plasma, serum and urine. In other embodiments, the sample is an environmental sample, a pharmaceutical sample or a food sample. In yet other embodiments, the sample is a fuel sample.

In some embodiments, the sample comprises cell lysate or tissue lysate.

In various embodiments, the sample is a crude sample.

In some embodiments, the porous membrane is an ultrafiltration membrane. In other embodiments, the porous membrane is a microporous membrane.

In some embodiments according to the methods of the claimed invention, the porous membrane comprises a polymeric material selected from the group consisting of PVDF (Polyvinylidene fluoride), PTFE (Polytetrafltioroethylene), hydrophilic PTFE and polyethylene. In a particular embodiment, a porous membrane comprises hydrophilic PTFE. However, it is contemplated that any suitable polymeric materials may be used in the methods according to the claimed invention. The selection of the polymeric material/membrane would be largely dependent on the analyte being quantitated. For example, it would be undesirable to use a polymeric material which absorbs at the same wavelength as the analyte of interest and/or interferes with the absorbance measurements.

In some embodiments, the porous membrane onto which a sample is spotted is contained within a device, referred to as a sample holder for convenience. In a particular embodiment, the sample holder is in the form of a card and is referred to as a sample holder card for convenience.

In various embodiments according to the claimed methods, the sample holder comprises a porous membrane which comprises an area within which the sample volume is contained on the membrane. In some embodiments, the area for sample containment comprises a hydrophilic region within a hydrophobic region, where the sample volume is contained within the hydrophilic region.

In some embodiments, the hydrophobic region is created by plasma treatment of a hydrophilic porous membrane. In other embodiments, the hydrophobic region is created by heat treatment of a hydrophilic porous membrane.

In some embodiments, the hydrophilic region includes one or more spots or one or more lines of hydrophobic regions.

It is important that the sample volume is contained with the diameter of the hydrophilic region. The diameter of hydrophilic region is dependent on the beam diameter of the IR instrument being used, where the beam passes through the sample contained within the hydrophilic region. In order to facilitate accurate quantitation, it is desirable to have the diameter of hydrophilic region to be smaller than or equal to the IR beam diameter. This ensures that the entire sample volume is visible to IR beam and that accurate quantitation is achieved.

In some embodiments, the diameter of the hydrophilic region of the sample holder ranges from 2.0 mm through 9.2 mm. In some embodiments, the diameter of the hydrophilic region ranges from 3.0 mm through 6 mm. In some embodiments, the sample volume which is spotted onto a membrane comprises a surfactant. In some embodiments, a surfactant is spotted onto a membrane before or after a sample volume is spotted onto the membrane.

BRIEF DESCRIPTION OF THE DRAWINGS

FIG. 8A depicts an open configuration of a fully assembled sample holder card and the two sides of a fixture. FIG. 8B depicts a closed cross-sectional schematic of a sample holder card and fixture assembly inside a vacuum plasma environment, where the area of the membrane on the sample holder card which is desired to be hydrophobic is exposed to plasma treatment, whereas the hydrophilic region on which a sample is spotted is protected from plasma treatment.

FIG. 14A depicts increased uniform sample distribution by chemical disruption when a detergent (SDS) is added to the sample. Cytochrome C (10 mg/ml), dissolved in both water and Phosphate Buffered Saline (PBS) was placed on a hydrophilic PTFE membrane (2 and 5 uL) and dried. The addition of SDS to the sample results in a more uniform distribution of sample (PBS+SDS not shown). FIG. 14B depicts physical disruption of sample distribution (by changing hydrophobic barriers) resulting in multiple "coffee rings" and more sample in the center of the sample area.

DETAILED DESCRIPTION OF THE INVENTION

Figure 1:
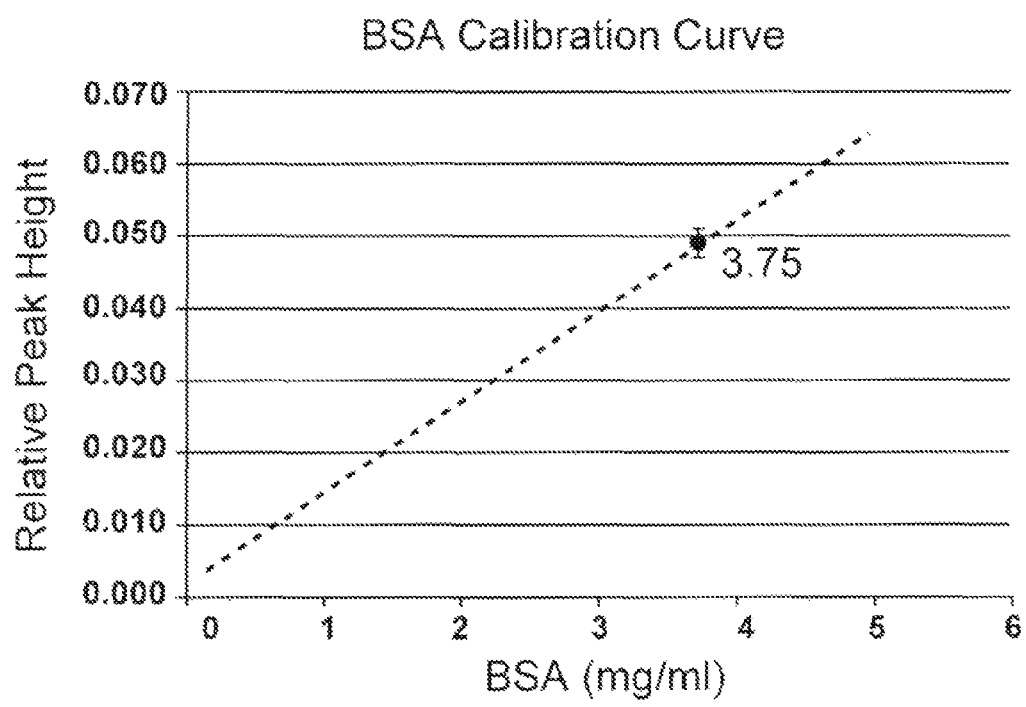
FIG. 1 is an exemplary calibration curve generated for use at future times. BSA was used to generate a calibration curve on one day (dotted line). A 4 mg/ml BSA sample was created days later (e.g., 4 days later in this case) and checked against the previously generated calibration curve.

The present invention provides improved methods for quantitation of one or more biomolecules in a sample using infrared spectroscopy (IR) as well as devices for use in the methods according to the claimed invention.

In order that the present disclosure may be more readily understood, certain terms are first defined. Additional definitions are set forth throughout the detailed description.

I. Definitions

The term "quantify," "quantitation," "quantitate," "measure" or "measurement," as used interchangeably herein, refers to the determination of amount or concentration of an analyte in a sample, using the methods according to the claimed invention. The term "analyte," as used herein, refers to any molecule of interest that is desirable to quantitate using the methods described herein. In various embodiments, an analyte is a biomolecule.

The term "biomolecule" as used herein, refers to any biological material of interest, which is desirable to quantitate using the methods according to the claimed invention. Exemplary biomolecules include proteins, peptides, nucleic acid molecules including DNA and RNA, lipids, carbohydrates and endotoxins (e.g., lipopolysaccharide). It is contemplated that any biomolecule may be quantitated using the methods according to the claimed invention, so long as the biomolecule is capable of absorbing in the infrared range of the electromagnetic spectrum.

The term "sample," as used herein, refers to any medium, which includes an analyte (e.g., a biomolecule) to be quantitated using the methods according to the present invention. A sample may include, but is not limited to, e.g., a food substance (e.g., poultry, fresh meat, milk, yogurt, dairy products, bakery products, beverages, beer, lemonade, juices, cheeses, vegetables, fruit, fish etc.), a water or sewage body (e.g., pond, lake, river, ocean, sewage canals, drinking tap water etc.), a clinical specimen (e.g., blood, plasma, serum, sputum, tissue, urine, saliva, sample/fluid from respiratory tract etc.), soil, and cosmetics and pharmaceuticals (e.g., lotions, creams, ointments, solutions, medicines, eye and ear drops etc.). In a particular embodiment, a sample comprises a cell or tissue lysate. In various embodiments of the claimed invention, a sample may constitute a crude sample, i.e., it does not require any preparation or treatment prior to use in the claimed methods.

In some embodiments, a small volume of a sample (e.g., 0.1-20 µl) is pipetted or spotted onto the hydrophilic region of a membrane contained in a sample holder (e.g., in the form of a card) and subsequently dried followed by exposing the sample to IR based spectroscopy. The sample volume on the card may be dried using any suitable method. For example, the sample volume may be air dried or dried using a convection heater or a conventional oven or even a microwave oven. It is contemplated that in some embodiments, a drying mechanism is incorporated into the IR system. In general, it is desirable that there are no traces of water present in a sample volume prior to quantitation as water may present a hindrance to obtaining accurate quantitation.

In some embodiments of the claimed methods, a membrane onto which a sample volume is spotted is subjected to a drying step followed by the use of infrared absorbance to detect the presence of water. If water is detected, the membrane is subjected to a drying step again and the drying step is repeated until the presence of water is undetectable. Typically, no further change in absorbance following a drying step is indicative that the presence of water is undetectable, or in other words, the sample is sufficiently dry for IR analysis.

The methods and devices according to the claimed invention enable the use of a very small sample volume to achieve accurate quantitation of an analyte in the sample. In various embodiments the sample volume is about 0.05 µl, 0.1 µl or 0.2 µl or 0.3 µl or 0.4 µl or 0.5 µl or 0.6 µl or 0.7 µl or 0.8 µl or 0.9 µl or 1.0 µl or 1.5 µl or 2 µl or 2.5 µl or 3 µl or 3.5 µl or 4 µl or 4.5 µl or 5 µl or 5.5 µl or 6 µl or 6.5 µl or 7 µl or 7.5 µl or 8 µl or 8.5 µl or 9 µl or 9.5 µl or 10 µl or 10.5 µl or 11 µl or 11.5 µl or 12 µl or 12.5 µl or 13 µl or 13.5 µl or 14 µl or 14.5 µl or 15 µl or 15.5 µl or 16 µl or 16.5 µl or 17 µl or 17.5 µl or 18 µl or 18.5 µl or 19 µl or 19.5 µl or 20 µl or greater than 20 µl. Although, the devices and methods described herein facilitate the use of very small volumes for quantitation of one or more biomolecules. In order to increase lower limit of detection and quantitation using the methods described herein, multiple aliquots of a sample volume can be applied to the sample holder card, with drying of the sample volume in between the aliquots. For examples, in case of samples containing very low levels of analytes, which may be difficult to detect or undetectable using the methods described herein, multiple aliquots of a certain sample volume (e.g., 10-20 µl) can be spotted on the sample holder card, with drying of the sample volume in between the different aliquots. Therefore, although, only a small volume of 10-20 µl is spotted onto the sample holder card in each application, a total sample volume of 50 µl to 100 µl or more could be applied in total over the multiple applications of the sample volume, with drying of each sample volume in between the applications.

In some embodiments, a sample volume of 100 µl or more is applied to the sample holder card by applying a 20 µl of sample volume to the card and drying the card. Once that sample volume is completely dry, additional 20 µl of sample volume can be applied to the sample holder card and the card can be dried again. This process can be repeated multiple times to spot the requisite sample volume on the card. The advantage of this technique is that it increases the limit of the analyte detection/quantitation.

As used herein, the term "lyse," "lysis" or "lysing" refers to any means by which a cell or tissue can be broken open, e.g., by compromising the cell membrane and possibly causing the contents of the cell to be liberated. Exemplary methods which may be used for lysing a cell or tissue include, but are not limited to, enzymatic methods, ultrasound, mechanical action (e.g., shear and impaction) and chemical methods.

As used herein, the term "nucleic acid" or "nucleic acid molecule" refers to any chain of two or more nucleotides, nucleosides, or nucleobases (e.g., deoxyribonucleotides or ribonucleotides) covalently bonded together. In some embodiments, a biomolecule which is quantitated using the methods according to the claimed invention is a nucleic acid molecule. Nucleic acid molecules include, but are not limited to, viral genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid molecule may be provided in a linear (e.g., mRNA), circular (e.g., plasmid), or branched form, as well as a double-stranded or single-stranded form. Nucleic acid molecules may include modified bases to alter the function or behavior of the nucleic acid, e.g., addition of a 3'-terminal dideoxynucleotide to block additional nucleotides from being added to the nucleic acid.

The term "wavelength," generally refers to the distance between one peak or crest of a wave and the next peak or crest. It is equal to the speed of the wave divided by its frequency, and to the speed of a wave times its period. Wavelength is a characteristic of both traveling waves and standing waves, as well as other spatial wave patterns. Wavelength is commonly designated by the Greek letter lambda ($\lambda$). Assuming that a sinusoidal wave is moving at a fixed wave speed, wavelength is inversely proportional to the frequency of the wave. Therefore, waves with higher frequencies have shorter wavelengths, and waves with lower frequencies have longer wavelengths.

The term "wave number," is a property of a wave proportional to the reciprocal of its wavelength. It is generally measured in units of $cm^{-1}$ and can be defined by the number of wavelengths per unit distance, i.e., $1/\lambda$, where $\lambda$ is the wavelength.

Figure 16:
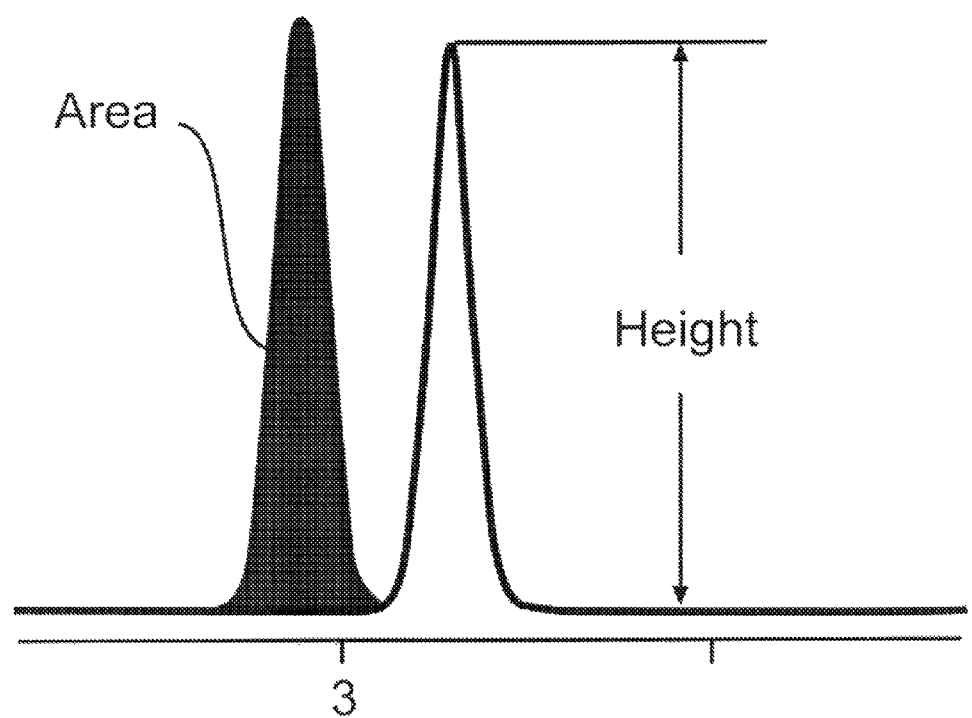
FIG. 16 is an infrared absorption spectrum, which depicts the area under one or more peaks, as calculated by drawing a baseline across the peak and measuring the area enclosed in the peak. The baseline is typically drawn based on points before and after the peak on the spectrum, as depicted in FIG. 16.

The term "absorption peak area" or "absorption peak areas" as used herein, refers to one or more parts of an infrared absorption spectrum observed following the exposure of a sample to IR spectroscopy, as described herein. Once an infrared absorption spectrum is obtained using the IR based methods described herein, the area under one or more peaks in the spectrum is calculated by drawing a baseline across the peak and measuring the area enclosed in the peak. The baseline is typically drawn based on points before and after the peak on the spectrum, as depicted in FIG. 16.

In some embodiments according to the claimed methods, a peak area correlates with the concentration or quantity of an analyte in a sample.

In some embodiments, the concentration of protein in a sample is measured as follows. As a first step, a calibration curve is generated using a calibrant, which includes protein standards of known concentration, and the calibration curve is pre-loaded onto an IR spectrometer instrument. The same calibration curve can subsequently be used each time that the instrument is used for quantitating protein in a sample. Further, it is not required that the calibrant be present in the sample being analyzed, or in other words, it could be derived from a completely different source than the sample. For example, in a particular embodiment, solutions of a protein standard such as, for example, BSA, are prepared in a buffer at various known concentrations. The standard solutions are applied to the hydrophilic region of a membrane in a sample holder in the form of a card, the membrane is dried and the absorption spectrum is measured using an IR instrument, e.g., the Bruker IR instrument. Without wishing to be bound by theory, it is contemplated that any suitable IR instrument may be used in the methods according to the present invention.

Most modern IR absorption instruments use Fourier-transform techniques with a Michelson interferometer. In some embodiments according to the claimed methods, in order to obtain an IR absorption spectrum, one mirror of the interferometer moves to generate interference in the radiation reaching the detector. Since all wavelengths are passing through the interferometer, the interferogram is a complex pattern. The absorption spectrum as a function of wavenumber ($cm^{-1}$) is obtained from the Fourier transform of the interferogram, which is a function of mirror movement (cm). This design does not have the reference cell of a dispersive instrument, so a reference spectrum is recorded and stored in memory to subtract from the sample spectrum.

Other exemplary IR absorption instruments include dispersive IR absorption instruments and single wavelength IR instruments. Dispersive IR spectrometers use diffraction grating in a monochromator in order to disperse the different wavelengths of light. In general, dispersive IR spectrometers have been replaced with FTIR instruments. Single wavelength IR instruments may be used for monitoring a single IR wavelength to measure the kinetics of a fast reaction.

In some embodiments according to the claimed invention, an FTIR instrument is used for the quantitation of one or more biomolecules. Area under the curve which encompasses amide I and amide II peaks (1800-1450 $cm^{-1}$) is calculated by the software inbuilt into the instrument. For example, the Bruker IR spectrometer includes the Bruker Opus software. A calibration curve is then set up which plots area under the peak vs. concentration of the protein standard. Using the calibration curve generated by the standard of known concentration, the concentration of an analyte in a sample is subsequently measured.

In general, a calibration curve refers to a graphical display of the functional relationship between the expected value of the observed signal to the analyte amount or concentration. Typically, standards encompassing a range of known concentrations of a calibrant are used to generate a calibration curve. The spectrum obtained with the sample is then compared with the standards to obtain the concentration of the desired analyte.

In some embodiments according to the methods described herein, the methods further include a step of monitoring/detecting absorption by water in the sample. Water absorbs at ~3400 and 1600 $cm^{-1}$, thereby overlapping with the spectrum obtained with many biomolecules. In some embodiments according to the present invention, an IR instrument is used which includes an in-built software to monitor the change in spectral intensity associated with absorption by water, which decreases as the amount of water in the sample reduces. Accordingly, by monitoring the spectral intensity associated with water, a user can determine if the sample needs to be further dried. Typically, the spectral intensity associated with absorption by water is measured a few times during the drying process, until the same spectral intensity is observed for 2 or 3 or more consecutive reads, thereby confirming that the sample is dry for the actual quantitation.

In some embodiments, a surfactant is included in the sample being analyzed using the methods of the invention. A surfactant may either be include in the sample being spotted onto a membrane or it may be added to the membrane before or after the sample is spotted. A surfactant, such as, e.g., sodium dodecyl sulfate (SDS) or Tween 20 or a chemical additive, e.g., Glycerol, reduces surface tension of a solution, thereby allowing for uniform distribution of sample within an area.

When an aqueous sample containing one or more biomolecules is dried on a hydrophilic PTFE substrate, a concentration gradient is formed as the sample dries. This deposition pattern results in the highest amount of sample being deposited in the outer most perimeter, and the lowest amount in the center of the sample area. This pattern is often referred to as a "coffee ring" or "donut" pattern. When the surface tension of the aqueous sample is reduced, such as with the addition of a surfactant, the deposition of the sample is more uniform across the total sample area. In the event in which the sample is being interrogated with an energy source, inclusion of a surfactant results in a more uniform distribution of the sample within the area being exposed to the energy source.

Exemplary surfactants include, but are not limited to, polyoxyethylene based non-ionic surfactants such as (Tween 20, Tween 40, Tween 60 and Tween 80). Anionic surfactants such as Sodium dodecyl sulphate (SDS), Ammonium lauryl sulphate, Sodium lauryl ether sulphate (SLES), Sodium stearate. In some embodiments, the concentration of a surfactant is about 1% or about 2% or about 3% or about 4% or about 5% or about 6% or about 7% or about 8% or about 9% or about 10%. In a particular embodiment, the concentration of a surfactant is about 5%.

Exemplary chemical additives include, but are not limited to polyols such as glycerol, ethylene glycol, propylene glycol, dipropylene glycol. In some embodiments, the concentration of chemical additive is about 1% or about 2% or about 3% or about 4% or about 5% or about 6% or about 7% or about 8% or about 9% or about 10%. In a particular embodiment, the concentration of a chemical additive is about 5%.

Also encompassed by the present invention are devices used for quantitation of one or more biomolecules in a sample using an IR based method as well as methods of making such devices. In some embodiments according to the present invention, a device used for quantitation of biomolecules is a sample holder in the form of a card which includes a porous membrane (e.g., an ultrafiltration membrane or a microporous membrane). In general, an ultrafiltration membrane is understood to have a pore size smaller than 0.1 µm.

In some embodiments, a porous membrane contained in a sample holder includes a hydrophilic region surrounded by a hydrophobic region. The hydrophilic region is the region of the membrane which is instantly wettable by water and the region where the sample is usually spotted or pipetted onto the membrane. It is also the region which is typically exposed to the IR beam.

In some embodiments, the hydrophilic region of the membrane is surrounded by a hydrophobic region, which is not wetted by water.

In some embodiments, the area for sample containment includes shapes/patterns of hydrophilic and hydrophobic regions, e.g., in the form of lines or spots of hydrophobic regions created within the hydrophilic region. Exemplary shapes and patterns are shown in FIGS. 8A-8D. Such shapes and patterns also enable a more uniform distribution of a sample within the area being exposed to the IR beam, just like the addition of a surfactant or a chemical additive.

Sample holder cards for use in infrared spectrophotometric analysis have been previously described in the art which include a microporous membrane, e.g., those discussed in U.S. Pat. Nos. 5,470,757 and 5,764,355, incorporated by reference herein in their entirety. However, there is no teaching of sample holder cards which include a hydrophilic area surrounded by a hydrophobic area for sample containment, as in case of the present invention. Further, these patents also do not describe sample holder cards and methods which demonstrate the improvements described here, e.g., quantitation of more than one biomolecule in a sample, use of a very small sample volume and no need for the generation of a calibration curve for each run etc.

The sample holder in the form of a card is typically manufactured from two layers of paper card stock laminated with adhesive to the membrane substrate. The sample holder could also be fabricated from any other substances such as plastic that can be adhered with an adhesive. Further, the sample holder could be constructed without any adhesive and be laminated via a coating on the card stock that adheres to the card stock when exposed to heat. In some embodiments, a sample holder is in the form of a card which is about 1.4 inches wide by 2.5 inches long and can hold at least 4 samples. However, a sample holder can be designed such that it can contain from 1 sample up to 96 samples or more (e.g., a 96-well plate format). A notch may be incorporated into the sample holder design, especially when it is in the form of a card. to orient the sample holder with the IR system in order to verify that the sample holder is inserted correctly into the carrier of the IR system to be exposed to an IR beam. It is also important that the sample holder be oriented correctly such that the IR beam passes through the hydrophilic region containing the sample.

The sample holder cards described herein are easy to manufacture, are cost effective and disposable.

This invention is further illustrated by the following examples which should not be construed as limiting. The contents of all references, patents and published patent applications cited throughout this application, as well as the FIGS., are incorporated herein by reference.

EXAMPLES

Example 1

Generation of Calibration Curve for Future Sample Quantifications

The methods of quantitating one or more biomolecules in a sample described herein obviate the need to generate a calibration curve, each time a quantitation experiment is run on an instrument. This is an improvement over the current assays in the art, where a user will typically be required to generate a new calibration or standard curve each time a quantitation assay is performed.

In methods described herein, a user generates a calibration or standard curve once and can use that for future analyses. In one experiment, a calibration curve was generated as follows. Solutions of various concentrations of analyte (BSA) were prepared in buffer and analyzed using FTIR based detection methods as described herein. The graph in FIG. 1 shows the peak area or peak height (Y axis) versus concentration or amount of analyte (X axis). The linear range of this calibration is used for calculation of concentration of an unknown sample when the peak area is known.

The typical equation is y=mx+c, where c=Intercept on Y axis, m=slope of the line; y=peak area or height, and x=concentration or amount of analyte. Additionally, the user can add data to the original calibration curve to increase the statistical relevance of quantification.

FIG. 1 is an example of a calibration curve that was generated, using various known concentrations of BSA in a buffer on one day, and a relevant sample of unknown concentration of protein quantitated days later against the same curve.

Example 2

General Protocol for Quantitation of a Biomolecule in a Sample

In a representative experiment, a sample containing one or more biomolecules (e.g., protein, nucleic acids, carbohydrates, lipids, etc.) is prepared in deionized water or a suitable buffer. Approximately 0.2-10 µl of a blank solution (e.g., deionized water or buffer alone) is applied to the hydrophilic region of the membrane contained in a sample holder, e.g., in the form of a card (referred to as a sample holder card herein). The same volume of the prepared sample solution is applied to one or more spots, which maybe present on the same sample holder card or on a different but identical sample holder card. The sample holder card is subsequently dried using one of the following techniques: heat (40-60° C., 0.5-2 minutes); compressed air/nitrogen or any other inert gas (0.5-$^2$ minutes) or a microwave oven. The dry sample holder card is subsequently inserted into the sample compartment of the IR instrument. The transmission/absorption spectrum of the blank solution is measured between 4000 and 400 $cm^{-1}$ in order to obtain a spectrum for the background followed by the measurement of the sample at the same wavelength range. Using a calibration curve which is inbuilt into the system and generated using standards at various concentrations, concentration of unknown sample is subsequently determined.

Figure 2:
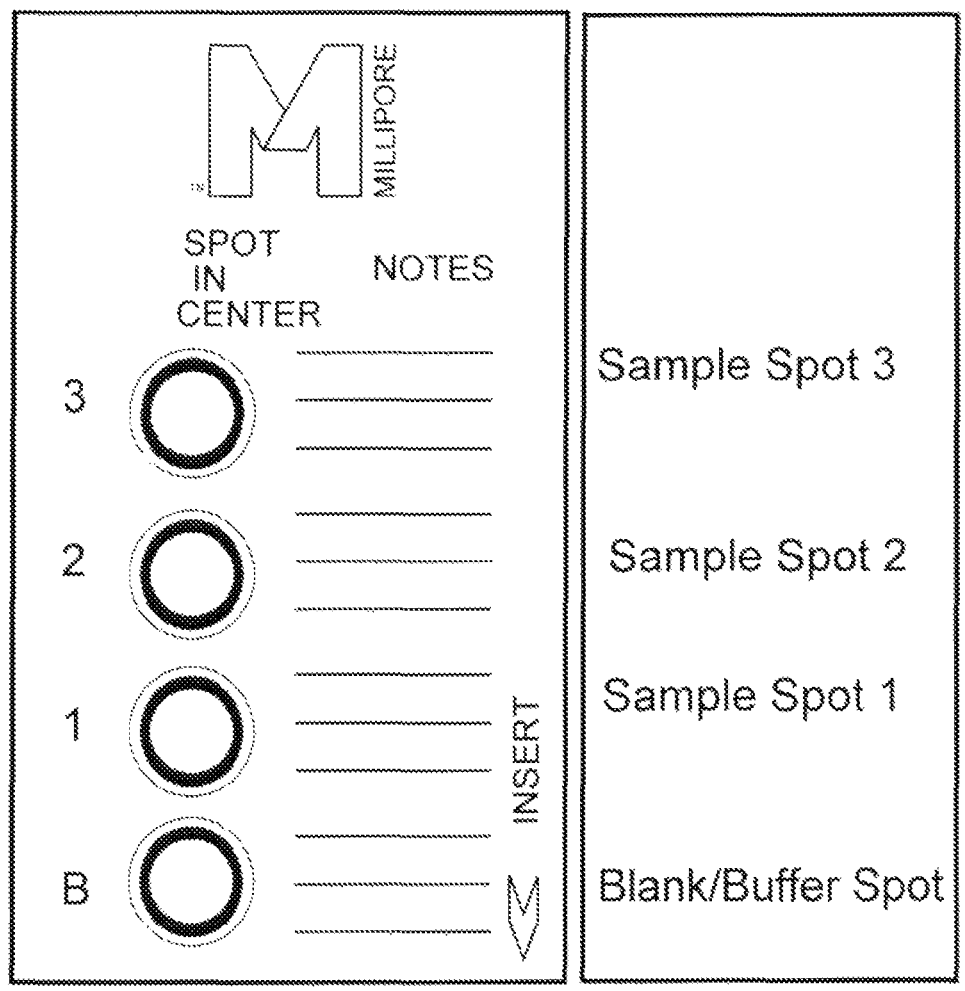
FIG. 2 is a schematic depiction of an exemplary sample holder according to the claimed invention. The exemplary sample holder is a card which includes 4 different membrane spots, each comprising a hydrophilic region surrounded by a hydrophobic region, for applying a volume of sample solution. Spots referred to as sample spot 1, 2 and 3, are meant for spotting a sample volume containing a biomolecule of interest in a suitable buffer, whereas, Spot B is used for spotting a volume of a blank solution or buffer alone. The sample volumes spotted onto spots 1, 2 and/or 3 could represent the same sample solution or constitute different sample solutions.

FIG. 2 depicts the image of an exemplary sample holder card which shows one spot for applying the blank (referred to as B) and spots for three samples (referred to as 1, 2 and 3). However, as discussed above, a sample holder card can be designed to have any number of spots for sample application.

Example 3

Quantitation of Protein and Nucleic Acid in a Sample Using IR Spectroscopy

In a representative experiment, both protein and nucleic acid in a sample were quantitated as follows using the methods according to the present invention.

In one experiment, bovine serum albumin (BSA; SIGMA Cat#A-7030) and deoxyribonucleic acids (DNA; Ambion Cat#AM9680 Sheared salmon sperm DNA) were mixed together in various proportions (10 to 1 µg in equal and inverse ratios) and dissolved in 1×PBS buffer. 1 µl samples were pipetted using a P10 Rainin pipette onto a hydrophilic PTFE membrane sample holder card, at positions 1, 2 and 3 of the sample holder card shown in FIG. 2. Same volume of the buffer in which the above sample was prepared was pipetted at position B on the sample holder card, as shown in FIG. 2.

Figure 3:
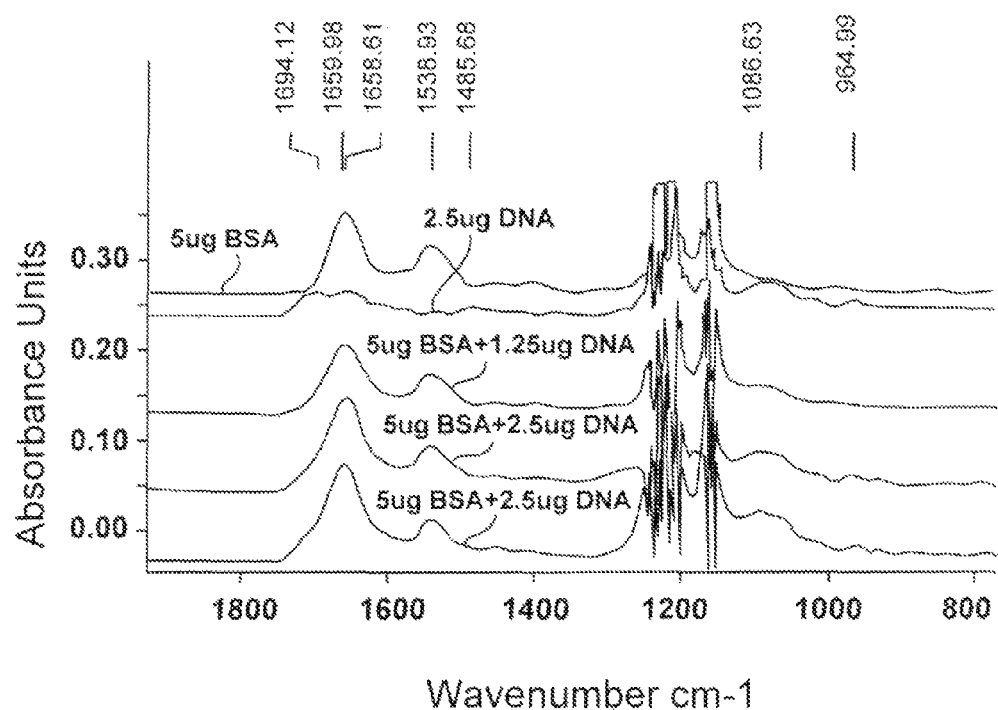
FIG. 3 is an infrared absorption spectrum depicting the results of a representative experiment to quantitate protein and nucleic acid in the same sample. The protein used in this experiment was BSA. The X-axis represents the wavenumber in $cm^{-1}$ and the Y-axis represents the absorbance units. The graph demonstrates that both DNA and protein (i.e., BSA) can be quantitated in the same sample using the IR based methods according to the present invention.

The sample holder card containing both the buffer and sample spots was dried using high pressure air. The sample holder card was inserted in the IR instrument and the absorption/transmission spectrum of the buffer was first measured between 4000 and 400 $cm^{-1}$. Subsequently, spectrum of the sample was measured using buffer spectrum as the background spectrum. The amount of protein and nucleic acids is determined using spectral range of 1700-1400 $cm^{-1}$ for proteins and 1740-1400 and 1120-940 $cm^{-1}$ for nucleic acids. It is to be noted that both proteins and nucleic acids absorb in the wavelength range of 1700-1400 $cm^{-1}$. Accordingly, once the concentration of nucleic acids is determined, it can be subtracted from the concentration of protein plus nucleic acids, as obtained using peak areas between 1700-1400 $cm^{-1}$, thereby providing concentration of protein alone. Thus, concentration of proteins and nucleic acids can be determined in a single experiment. In this experiment, calibration curves were generated independently for proteins and DNA using pure samples of protein and DNA dissolved in a buffer or deionized water. The results of one such experiment are depicted in FIG. 3.

Example 4

Quantitation of Peptides in a Sample Using IR

Figure 4:
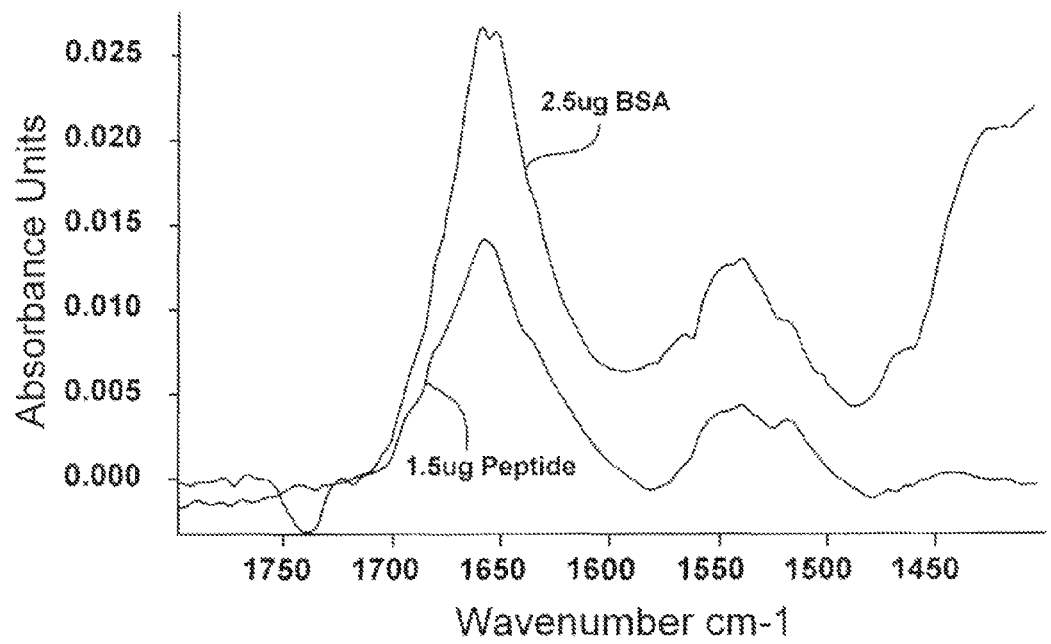
FIG. 4 is an infrared absorption spectrum depicting the results of a representative experiment to quantitate peptide in a sample. BSA was used as a protein standard in this experiment for quantitation. The X-axis represents the wavenumber in $cm^{-1}$ and the Y-axis represents the absorbance units.

In another representative experiment, it is demonstrated that the methods according to the present invention could be used for quantitating peptides. In one experiment, a peptide sample was dissolved in water to a 1 mg/ml concentration. 2 µl volume of the samples were pipetted using a P2 Rainin pipette onto a hydrophilic PTFE membrane containing sample holder card, as depicted in FIG. 2, and dried in a 40° C. heater. The same sample holder card also contained a position called blank (B), where 2 µl volume of the water in which sample is dissolved was pipetted. The card was inserted in the IR instrument and the absorption/transmission spectrum of the water/buffer blank was measured followed by the measurement of the samples using the water/buffer spectrum as the background. The amount of peptide was determined using spectral range of 1700-1400 $cm^{-1}$. Calibration curve was generated using pure samples of BSA as a calibrant in buffer/water. The results of one such experiment are depicted in FIG. 4.

Example 5

Quantitation of Lipopolysaccharides in a Sample Using IR

Figure 5:
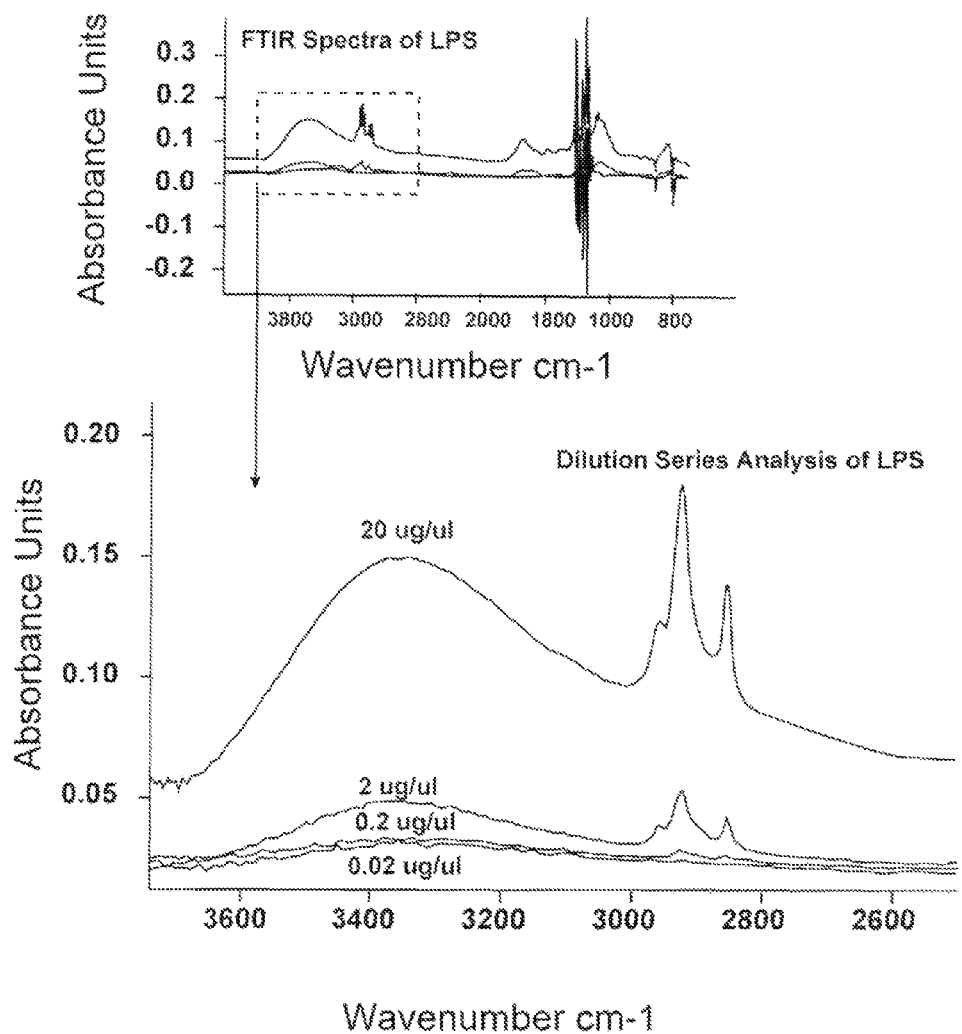
FIG. 5 is an infrared absorption spectrum depicting the results of an experiment to quantitate a lipopolysaccharide (LPS) in water, which is an endotoxin. The X-axis depicts the wavenumber in $cm^{-1}$ and the Y-axis depicts the absorbance units. The spectrum demonstrates that the spectral intensity decreases as the concentration of LPS in water decreases from 20 μg/μl to 0.2 μg/μl. Further, a calibration curve using LPS is generated using this experiment and used for subsequent quantitation of endotoxins.

In a representative experiment, the methods according to the present invention were used to quantitate a lipopolysaccharide in a sample. Specifically, a lipopolysaccharide such as an endotoxin, (Lipopolysaccharide (LPS); SIGMA L2630), was dissolved in a 1×PBS buffer to obtain a 20 mg/ml stock solution. 2 µl volume samples were pipetted using a P2 Rainin pipette onto a hydrophilic PTFE membrane containing sample holder card, as depicted in the image in FIG. 2, and dried using a 40° C. heater. The same sample holder card also contained a position called blank (B), where a 2 µl volume of the buffer in which sample is dissolved is applied. The sample holder card was inserted in the IR instrument and the spectrum of the buffer was first measured followed by the spectrum of the sample, which regards the blank buffer spectrum as the background spectrum. A titration of LPS dilutions were recorded based on stock solution calculation in order to obtain a calibration curve. The results of one such experiment are depicted in FIG. 5.

Example 6

Monitoring the Presence of Water in a Sample Using IR

The methods described herein can also be used for detecting the presence of water in a sample. It is largely undesirable to have water in a sample being analyzed using IR based methods as water can affect the accuracy of quantitation of biomolecules, for example, especially in the case of protein/peptide quantitation.

In a representative experiment, 2 µl of a 10 mg/ml BSA (Sigma Cat #A-7030) solution in Milli Q water was applied to the hydrophilic region of the membrane contained in a sample holder, e.g., in the form of a card (referred to as a sample holder card herein).

The wet sample was then placed within the IR beam of a IR spectrometer and IR absorption spectrum was measured. The absorption spectra are recorded as the signal intensity and the signal profile change, for example, due to evaporation of water.

Figure 6:
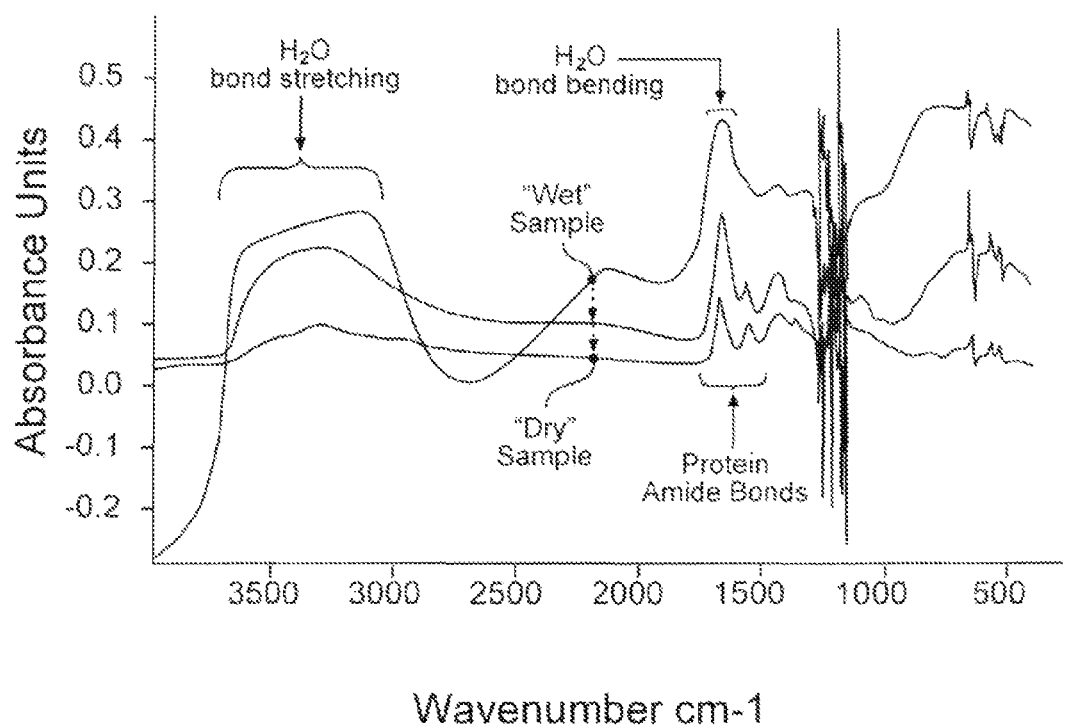
FIG. 6 is an infrared absorption spectrum depicting the results of an experiment to monitor/measure/detect the presence of water in a sample. The X-axis depicts the wavenumber in $cm^{-1}$ and the Y-axis depicts the absorbance units. As depicted in the spectrum, when water is present in the sample, there is spectral interference from the vibrational bond stretching and bending associated with the —OH bonds of water, which interferes with the resolution of protein amide bonds. However, as the sample is dried and the water evaporates, the spectral intensity associated with water decreases, as also depicted in the spectrum.

When the signal intensity for the absorption spectrum remains constant over 3 consecutive measurements, the sample is regarded dry and the software (e.g., the Opus software in case of the Bruker instrument) collects the absorption spectrum of BSA between 4000-400 cm-1 and using an inbuilt calibration curve determines the concentration of BSA in that solution. The results of one such experiment are depicted in FIG. 6, which shows a decrease in signal intensity associated with water as the sample is dried.

Example 7

Effect of a Surfactant on the Distribution of Sample

Aqueous solutions can have a problem with drying uniformly and obtaining a uniform distribution on the area of the membrane being exposed to an IR beam.

This experiment demonstrates that the addition of a surfactant to a sample solution results in a uniform distribution of the sample on the area being exposed to the IR beam and consequently more accurate quantitation. In a representative experiment, a 5 µl of 10 mg/ml Cytochrome C protein sample solution was used, which was dissolved in PBS and dried with and without 5% SDS. The sample was spotted onto a sample holder card and placed within an IR beam with a total diameter of 4.5 mm.

Figure 7:
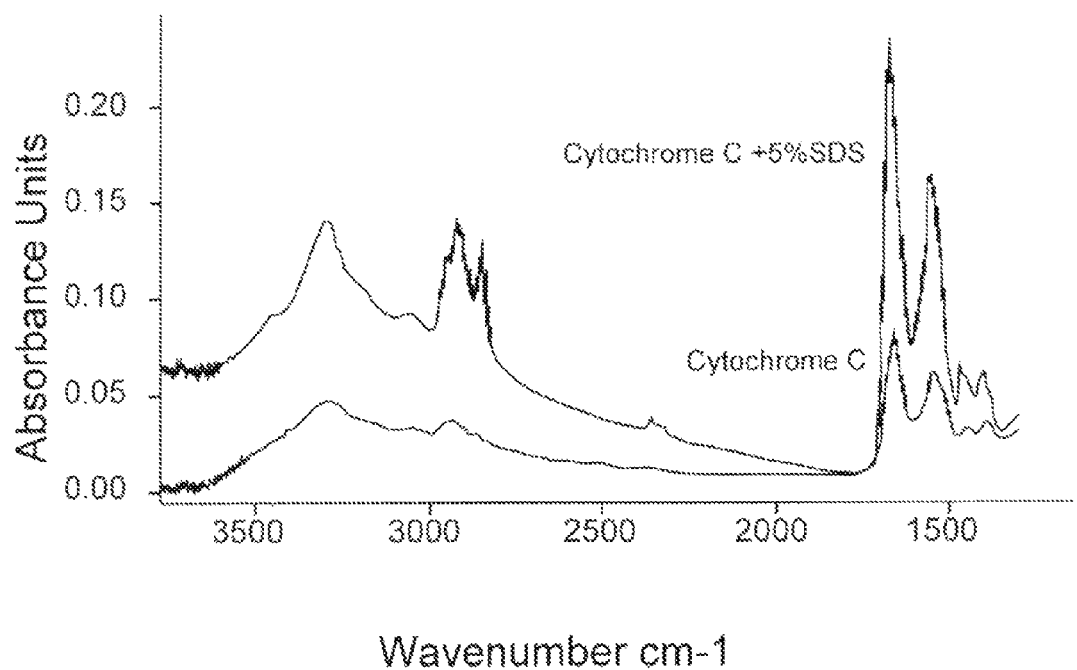
FIG. 7 depicts a graph demonstrating a more even distribution and absorption profile of a sample, when a surfactant (e.g., SDS) is added to the sample. The X-axis depicts the wavenumber in $cm^{-1}$ and the Y-axis depicts the absorbance units.

It was observed that only about 10% of the sample without SDS was absorbing the IR beam since most of the sample was contained in the outer 1 mm of the sample area. However, in the sample in which SDS was present, a more uniform distribution of the sample resulted in more absorption of the IR since the sample was within the maximum irradiance ($l/e^2$) of the beam. The integrated amide 1 and 2 peak area (1725 to 1479 $cm^{-1}$) was about 3-fold higher than that of the sample without SDS. The results of one such experiment are depicted in FIG. 7. The X axis in this IR absorption spectrum depicts the wavenumber ($cm^{-1}$) where as the Y axis depicts the absorbance units.

Example 8

Manufacture of a Sample Holder Card Using Plasma Treatment for Sample Containment Also encompassed by the present invention are sample holders that may be used in the methods for quantitating one or more biomolecules in a sample, as described herein. In some embodiments, a sample holder is in the form of a card, and is referred to as a sample holder card for convenience. It is imperative that the sample holder cards are able to contain the sample within the IR beam in order to obtain an accurate absorption spectrum and consequently quantitation of the one or more biomolecules of interest.

In one method of manufacturing a sample holder card for use in the methods according to the present invention, a vacuum plasma environment was used for generating an area for sample containment. The starting membrane used in the sample holder card was a hydrophilic PTFE membrane, which is sold by Sumitomo under the brand name Poreflon. The membrane comprises pores of a size averaging 0.03 µm (HHPSW-005-30) and is coated with hydrophilization treatment to impart a water wettable surface. Exposing the Poreflon hydrophilic membrane to a vacuum plasma environment cleans the treatment from the surface exposing the naturally hydrophobic PTFE.

Figure 8A:
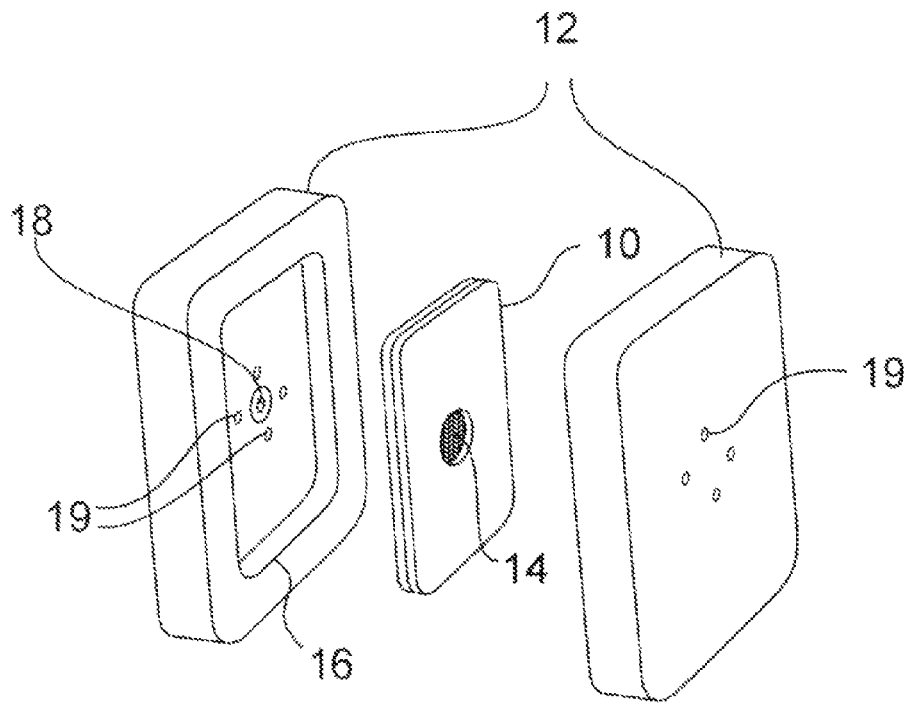
FIGS. 8A and 8B depict open and closed views, respectively, of a fixture and sample holder card assembly for use in a plasma based sample containment.
Figure 8B:
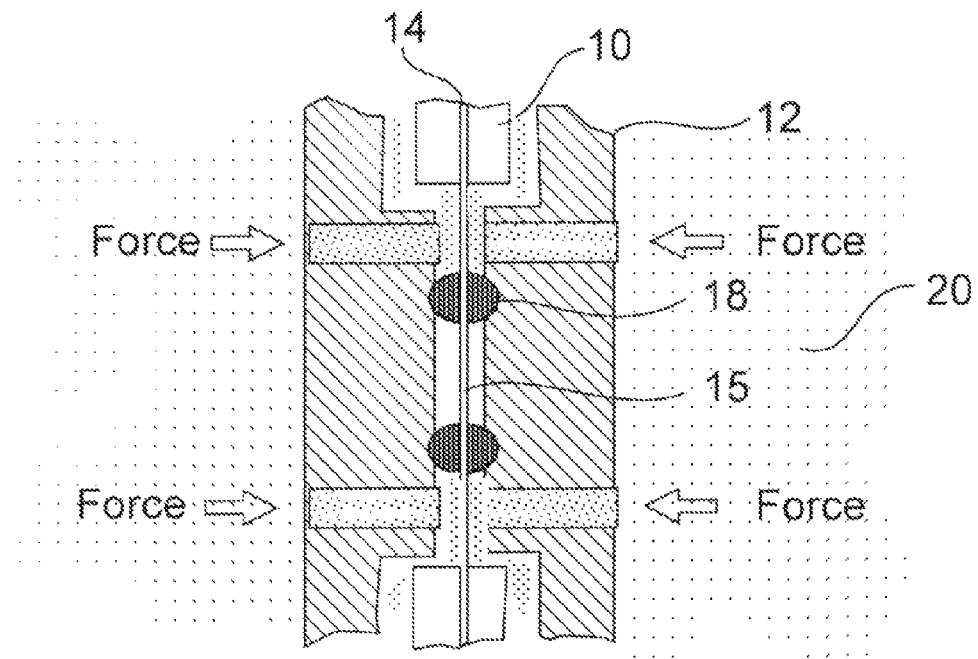

FIGS. 8A and 8B depict the experimental open and closed views, respectively, of a masking fixture within which an assembled sample holder card is placed for exposure to plasma. The membrane was fabricated into a card consisting of two rigid adhesive coated paper sheets which had a 12.5 mm through hole in the center of each. The two paper sheets were assembled with the Sumitomo hydrophilic membrane sandwiched there between, thereby covering the hole in the assembled paper card. The assembled card (10) is shown in FIG. 8A, with the fixture (12) in an open configuration. The assembled card (10) containing the hydrophilic membrane (14) was positioned in the masking fixture (12) containing a frame (16) for centering the card, as depicted in FIGS. 8A and 8B. Elastomeric seals (18) were present at the opposite sides of the centered and positioned membrane card (10). Surrounding the elastomeric seals (18) are four holes (19), which provide communication for the plasma gas to access the membrane (14) to be treated. The masking fixture (12) was subsequently closed, as depicted in a cross-sectional view in FIG. 8B, so that the elastomeric seals (18) are compressively sealed against the opposite sides of the membrane (14) in the card (10). A force, e.g., by way of clamps, was used for closing the fixture (12) on to the sample holder card (10) containing the hydrophilic membrane (14).

The card (10) positioned in the fixture (12) was subsequently placed into a vacuum plasma environment, the closed cross-sectional view of which is depicted in FIG. 8B. An exemplary vacuum plasma system which may be used is the Harrick Vacuum Plasma system Model PDC-001. The chamber (20) inside the system was evacuated of gas using a vacuum pump (not shown). Atmospheric gas was introduced into the chamber (20), and maintained at a flow rate of approximately 2-5 cc/min. The power to an RF generator (not shown) was applied and maintained for a period of time ranging from 10 seconds to 7 minutes. The region of the membrane (15) of the sample holder card (10) between the elastomeric seals (18) was protected from plasma, whereas the remaining outside was exposed to plasma, which is depicted by dots.

The plasma exposure experiment using the fixture described in FIGS. 8A and 8B showed that any processing time greater than 1 minute resulted in a clear definition of hydrophilic and hydrophobic region with a sharp transitional edge occurring at the position of the elastomeric seals (18). Less the 1 minute plasma processing times resulted in a blurry transition edge to no transition edge at all, resulting in a membrane remaining hydrophilic and the sample that was not contained.

Figure 9:
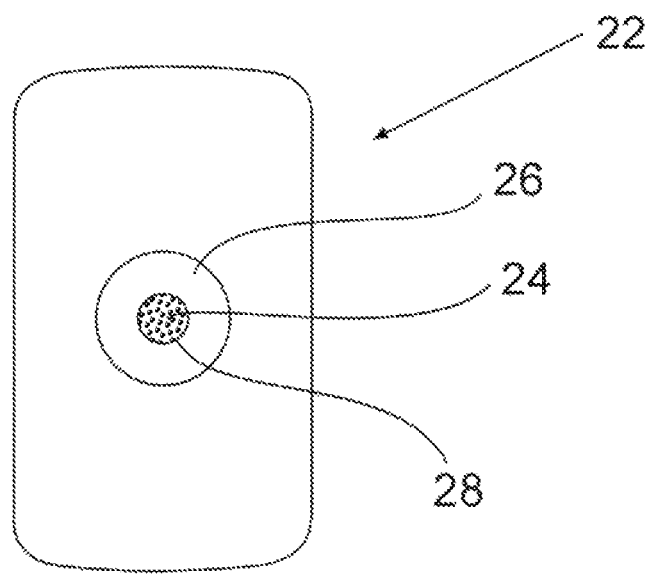
FIG. 9 depicts the schematic of a sample holder card subsequent to plasma treatment. The hydrophilic area represents the protected region of the membrane, which is surrounded by a hydrophobic area which was exposed to plasma treatment.
Figure 10A:
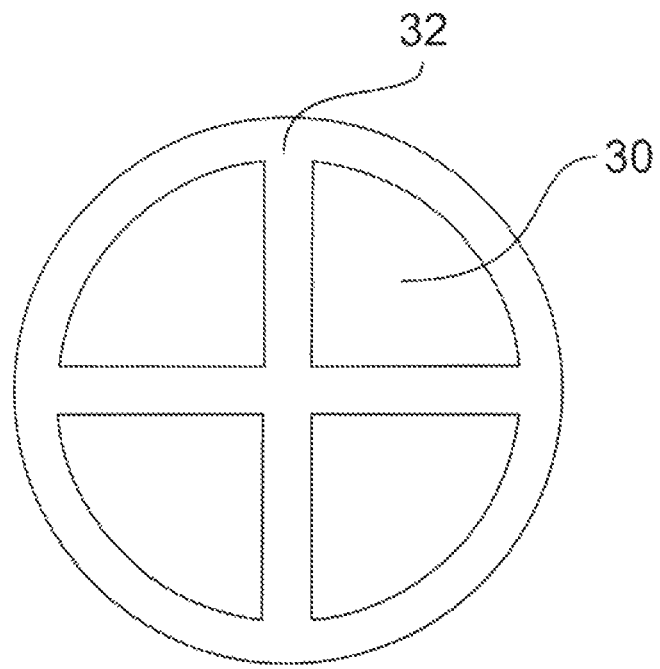
FIGS. 10A-10D depict exemplary shapes/patterns of hydrophobic and hydrophilic regions within a membrane of a sample holder card, which may be created by suitably positioning the elastomeric seals (in case of plasma treatment method) or by shape of the heated platen (in case of the heat treatment method).
Figure 10B:
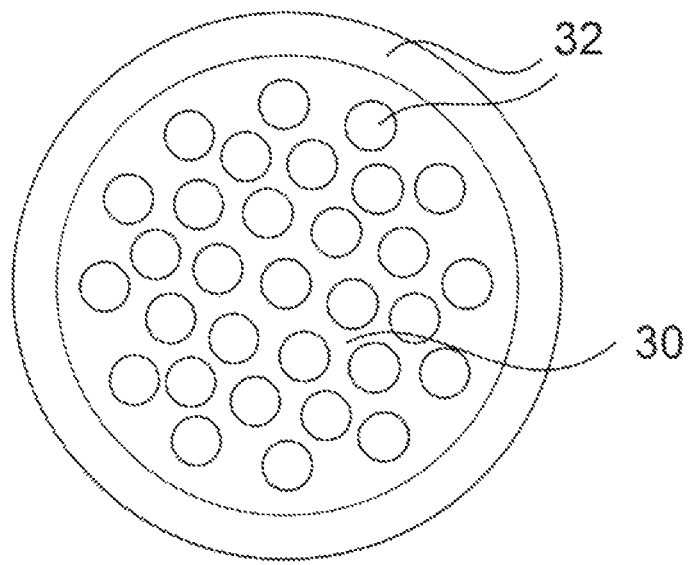
Figure 10C:
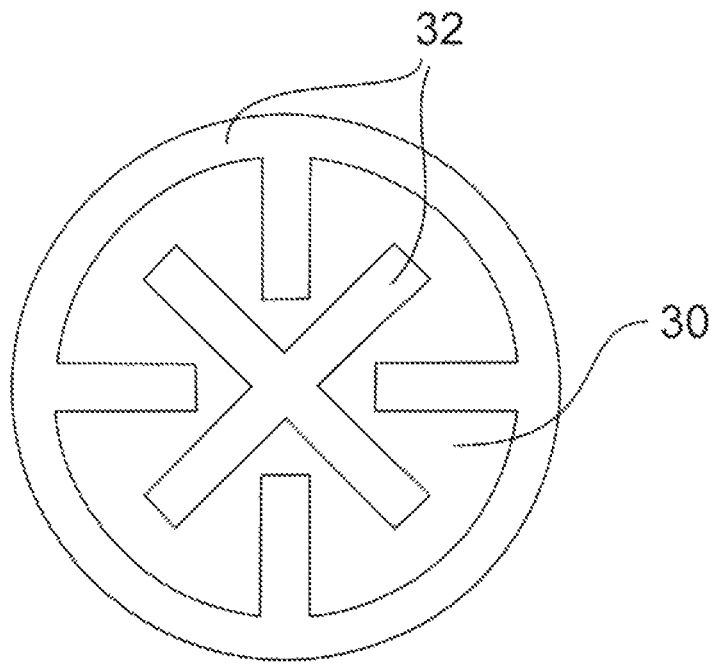
Figure 10D:
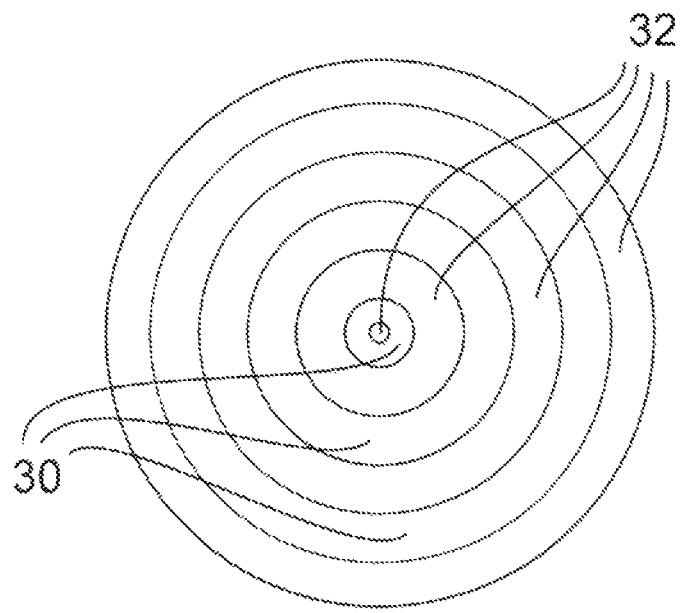

FIG. 9 depicts an exemplary sample holder card (22) containing a membrane having a hydrophilic region (24) surrounded by hydrophobic region (26) made using the method described in this Example. The border between the two regions is a transitional edge or line (28).

As discussed above, it is further desirable to have the sample distributed as uniformly as possible within the IR beam. One way of achieving a uniform distribution is the addition of a surfactant to a sample, as discussed above. Another way of achieving a uniform distribution is to create patterns/shapes of hydrophobic areas interspersed with hydrophilic areas on the membrane, as discussed herein.

It is understood that a drying drop will deposit the sample preferentially along the outer edge of the drying drop such as is commonly observed with the coffee ring phenomena. To minimize this drying pattern, the hydrophobic region surrounding the hydrophilic region can be further modified. This may be achieved, for example, by suitably positioning the elastomeric seals on the membrane in a manner which results in a pattern on the membrane of hydrophobic spots or lines within a hydrophilic area. Such a pattern is expected to result in multiple smaller drops thereby creating smaller and smaller drying patterns. These smaller drying patterns deposit the sample in a more uniform configuration within the IR beam. It is understood that the possible shapes/patterns which may be configured onto the membrane can be in the form of lines, dots, star shapes and other common shapes. Further, the outer hydrophobic region can also a shape such as a star shape, a square shape etc. Exemplary hydrophobic/hydrophilic patterns which may be generated by suitably positioning the elastomeric seals on the fixture are depicted in FIGS. 10A-10D. Hydrophilic regions are shown by the numeric reference 30 and the hydrophobic regions are shown by the numeric reference 32.

Example 9

Manufacture of Sample Holder Card Using Heat Treatment for Sample Containment

In another experiment, a sample holder card for use in the IR methods according to the present invention was manufactured as follows, using heat treatment as another alternative means for achieving sample containment on the membrane in the card.

In an exemplary experiment, the surface wettability of a hydrophilic PTFE membrane was altered by exposure to a heated platen, in order to create a region for sample containment. The hydrophilic PTFE membrane that was used is sold by Sumitomo under the brand name Poreflon, has a pore size averaging 0.05 μm pores (HHPSW-005-30) and is coated hydrophilization treatment to impart a water wettable surface. In general, using the methods described in this example, any Poreflon membrane with pore size ranging from 0.05 μm-0.45 μm and the thickness ranging between 30 μm through 80 μm can be-modified using a heated platen.

Figure 11:
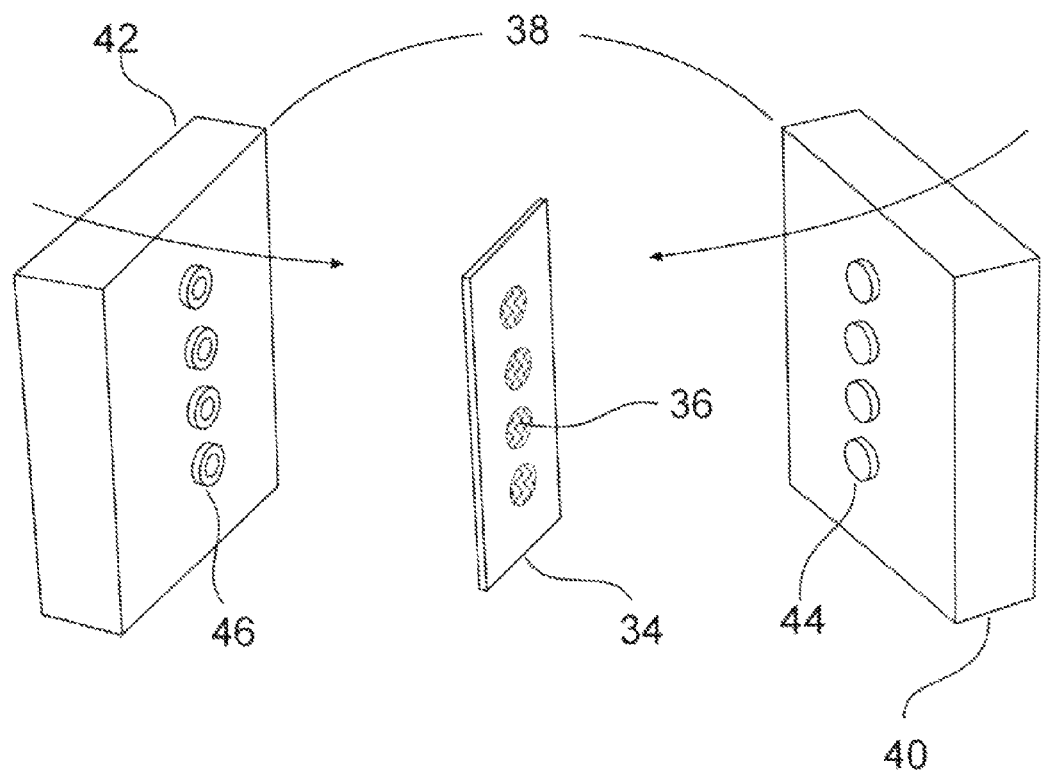
FIG. 11 is an expanded view of an embossing fixture and sample holder card system for generating a hydrophobic sample containment area within the membrane, including a heated platen and a silicone base.

As in case of Example 8, the hydrophilic PTFE membrane was fabricated into a card consisting adhesive coated paper sheets which had four (4) 10 mm through holes. The two paper sheets were assembled with the Sumitomo hydrophilic membrane sandwiched between the sheets, thereby covering the holes in the assembled paper card. This assembled card (34) containing a hydrophilic membrane (36) was positioned into an embossing fixture (38) which contains a pneumatic cylinder (not shown) attached to cal-rods (not shown) and a heated platen (42), as depicted in FIG. 11. The cylinder positions the heated platen (42) on or above the membrane (36) in the sample holder card (34) and elastomeric pads (44) on nest (40) supports the underside of the membrane (36). The heated platen (42) contains raised bosses (46) and the nest (40) contains elastomeric pads (44), which align with the raised bosses (46), when the sample holder card (34) is placed there between, which results in the regions that are in direct contact with the heated platen (42) to become hydrophobic.

Figure 12A:
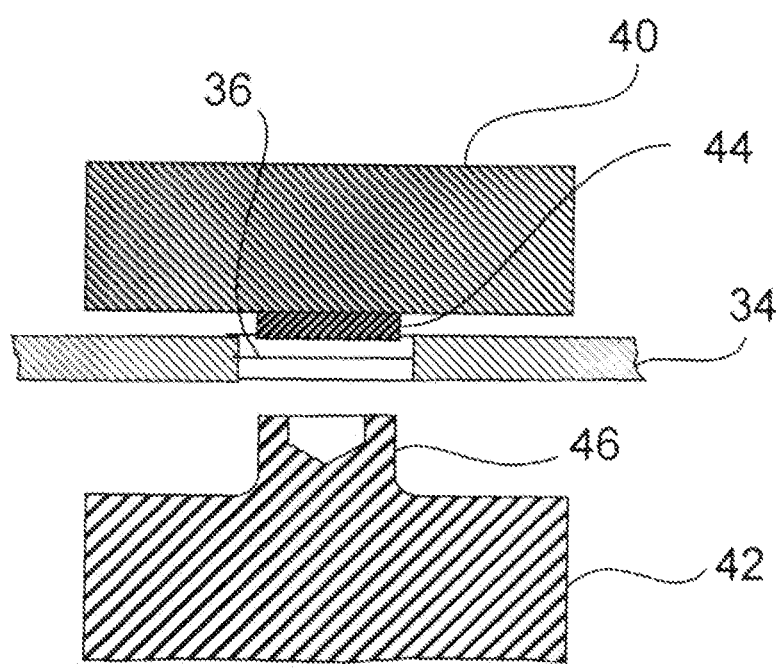
FIGS. 12A and 12B depict open and closed cross-sectional views, respectively, of an embossing head/heated platen system, after the sample card holder is placed in the system.
Figure 12B:
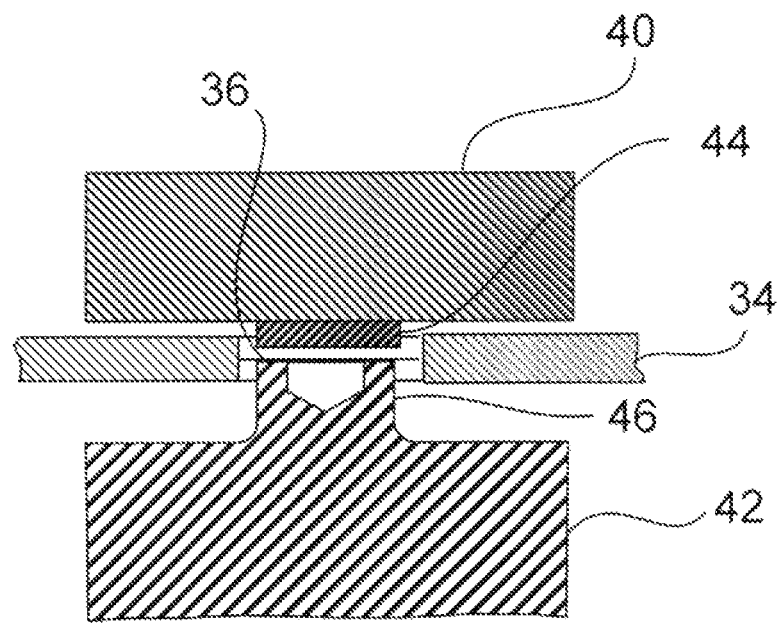

Open and closed cross-sectional views of the embossing fixture/card/heated platen assembly are depicted in FIGS. 12A and 12B, respectively.

After the heated platen (42) was exposed to the membrane (36) for a fixed amount of time (e.g., 5 seconds to 5 minutes), the cylinder (not shown) moved the heated platen (42) away from the membrane card (34).

As also in case of Example 8, the shape of contained area may be modified. In case of the heat treatment, the shape of the contained area can be controlled by the shape of the raised bosses and elastomeric pads that are in close proximity to the membrane, such that the portions of the membrane in contact with the raised bosses of the heated platen become hydrophobic, whereas the portions that do not come in contact with the heated platen remain hydrophilic.

Figure 13A:
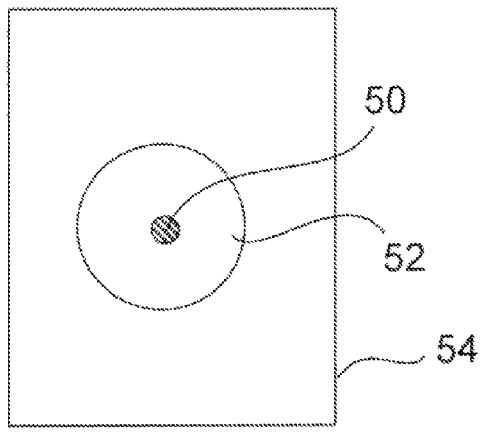
FIGS. 13A-13D depict the results of an experiment to show that a membrane retains a sample (e.g., water) within the sample containment area subsequent to heal treatment, as shown in FIG. 13C (at 0 seconds) and FIG. 13D (at 30 seconds) relative to a membrane that was not subjected to heat treatment, as shown in FIG. 13A (at 0 seconds) and FIG. 13B (at 30 seconds).
Figure 13B:
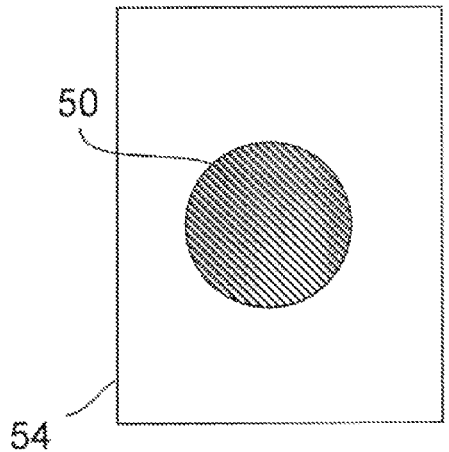
Figure 13C:
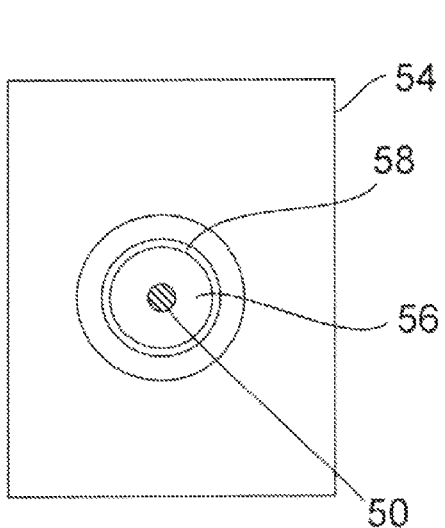
Figure 13D:
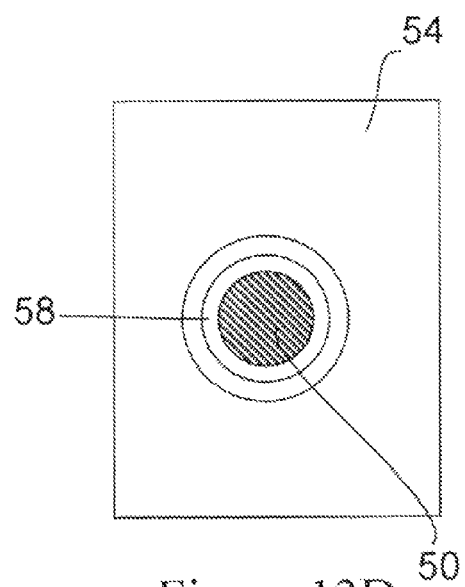

In order to confirm that the hydrophobic area generated using either plasma treatment described in Example 8 or using heat treatment described in the current Example, was effective in containing the sample, the sample containment properties of both heat or plasma treated and untreated membranes were investigated using water as a sample. FIGS. 13A-13B depict the sample containment properties of a membrane not subjected to heat or plasma treatment and FIGS. 13C and 13D depict the sample containment properties of a membrane which was subjected to either heat treatment or plasma treatment. A 2 μl volume of water as a sample (50) was spotted onto the hydrophilic membrane (52) of a sample holder card (54). FIG. 11A depicts the water sample (50) at time zero and FIG. 12B depicts the water sample (50) at time 30 seconds. As shown in FIG. 13B, the water sample spread throughout the membrane area, which resulted in the wetted area being wider in diameter than the diameter of an IR beam. Whereas, in case of the heat treated membrane or plasma treated membrane, as depicted in FIGS. 13C and 13D, both at time zero (FIG. 13C) as well as at 30 seconds (FIG. 13D), the water sample (50) was contained within the hydrophilic region (56) of the membrane surrounded by a hydrophobic barrier region (58). Accordingly, heat or plasma treatment, as described herein, may be used for generating an inner hydrophilic region (56) surrounded by an outer hydrophobic barrier region (56).

Example 10

Uniform Distribution of Sample Via Chemical or Physical Disruption

It has been observed that, drying of an aqueous biological sample for FTIR analysis often results in an uneven sample distribution pattern, with the highest concentration of sample on the outer edge of the sample area, thereby forming a so-called "coffee Ring" or "donut ring" pattern, which can result in inaccurate quantitation.

Figure 14A:
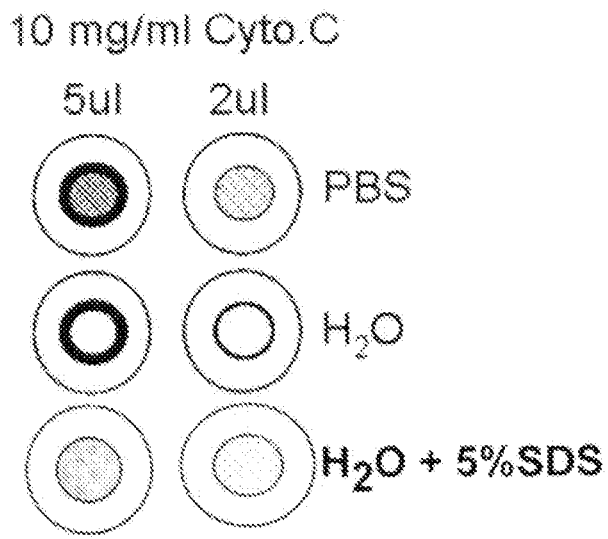
FIGS. 14A and 14B depict the effects of chemical and physical disruption, respectively, on the "coffee ring" deposition pattern of sample.
Figure 14B:
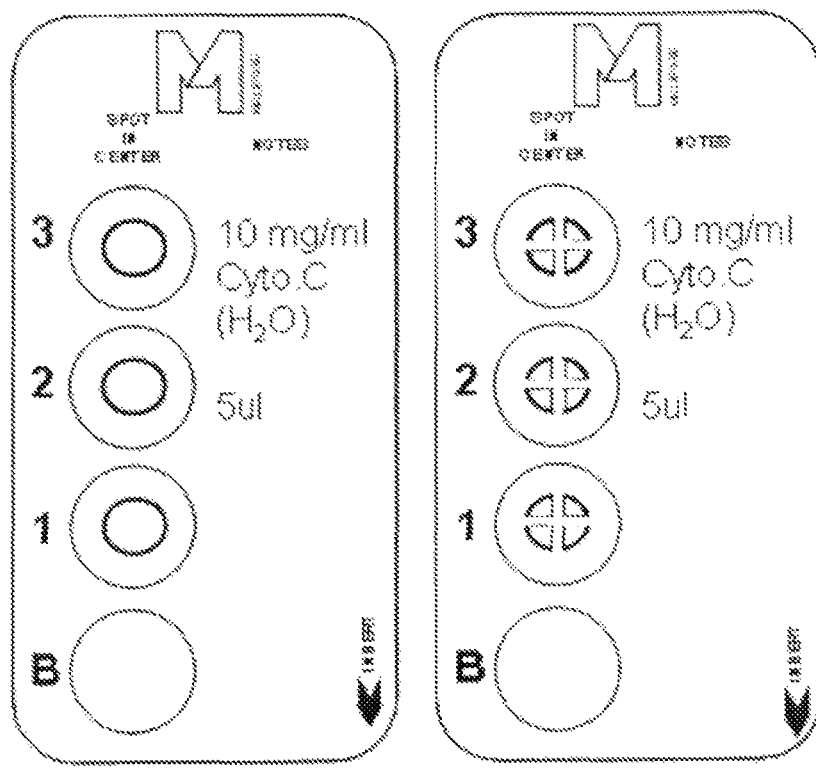

In a representative experiment described herein, the use of a surfactant or a detergent resulted in a more uniform distribution of sample by causing the sample to dry in a more uniform pattern in the sample containment area, as depicted in FIG. 14A. Also, the addition of a hydrophobic barrier-pattern (e.g. "X" cross pattern) in the sample area can cause the sample to dry more toward the center of the sample area, as depicted in FIG. 14B, resulting in a sample distribution close to the effects of using a surfactant additive. Distribution of the sample or disruption of the 'coffee ring' resulted in higher concentration and lower percent coefficient of variation (% CV).

Examples of surfactants that can be used include, but are not limited to, Tween 20 and sodiumdodecylsulfate (SDS). In one experiment, the ring-pattern of a dried cytochrome C sample was shown to vary based on the solution in which the sample was dissolved (e.g., PBS versus $H_2O$). The differences in the sample distribution within the IR beam can influence the transmission of the IR beam through the sample. In order to disrupt the ring-pattern, resulting in a more uniform distribution of sample, detergents or surfactants can be added to the sample, or directly to the membrane on which the sample is spotted and dried.

In Table 1 below, the amide 1&2 peak area of Cytochrome C protein were calculated in the absence ($H_2O$ only) and presence of SDS (1 and 5%). The addition of SDS resulted in an increase of calculated sample area as well as a decrease in percent coefficient of variation (% CV) (e.g., from 9.1 to 2.3%).

Figure 15:
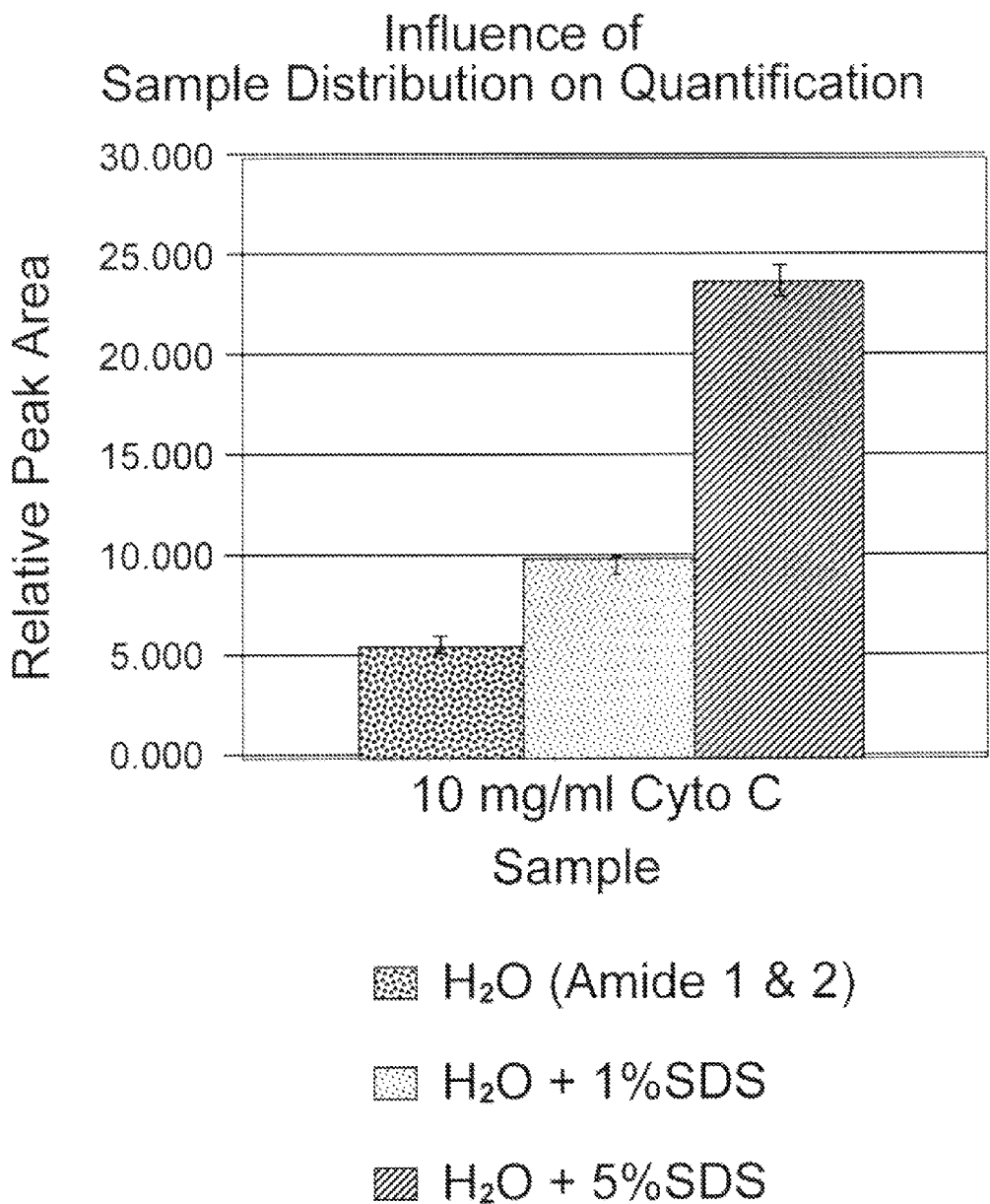
FIG. 15 is a bar graph depicting the effect of addition of SDS to a sample. SDS (1 and 5%) was added to Cytochrome C samples and dried. Addition of SDS resulted in an increase in respective peak area.

FIG. 15 depicts a bar graph representation of the tabulated data, shown in Tables 1 and 2 below. The increase in sample value and decrease in % CV with the addition of SDS is due to a more uniform distribution of sample (more sample is within the total IR beam) and less variability is present between samples (even distribution of sample versus differences in case of ring-formation).

The Amide 1 and 2 peak areas in Tables 1 and 2, column B, were calculated using OPUS 6.5 software (Bruker). The average value was calculated as well as the % CV. SDS (1 and 5%) was added to the samples and the peak area and % CV were reanalyzed.

TABLE 1

| Protein | Amount [mg/ml] | Volume (ul) | Additive | Amount (%) | Sample | B Amide 1 & 2 | |
|---|---|---|---|---|---|---|---|
| Cytochrome C | 10 | 2 | dH2O | | 1 | 6.137 | |
| Cytochrome C | 10 | 2 | dH2O | | 2 | 5.225 | |
| Cytochrome C | 10 | 2 | dH2O | | 3 | 5.309 | |
| | | | | | | 5.557 | =Average |
| | | | | | | 0.504 | =Std dev |
| | | | | | | 9.1 | =% CV |
| Cytochrome C | 10 | 2 | SDS | 1 | 1 | 9.969 | |
| Cytochrome C | 10 | 2 | SDS | 1 | 2 | 9.525 | |
| Cytochrome C | 10 | 2 | SDS | 1 | 3 | 9.802 | |
| | | | | | | 9.765 | =Average |
| | | | | | | 0.224 | =Std dev |
| | | | | | | 2.3 | =% CV |
| Cytochrome C | 10 | 2 | SDS | 5 | 1 | 24.156 | |
| Cytochrome C | 10 | 2 | SDS | 5 | 2 | 24.045 | |
| Cytochrome C | 10 | 2 | SDS | 5 | 3 | 22.745 | |
| | | | | | | 23.649 | =Average |
| | | | | | | 0.785 | =Std dev |
| | | | | | | 3.3 | =% CV |

TABLE 2

| Protein | Amount [mg/ml] | Volume (ul) | Modification | Sample | Amide 1 & 2 | |
|---|---|---|---|---|---|---|
| Cytochrome C | 10 | 5 | | 1 | 21.352 | |
| Cytochrome C | 10 | 5 | | 2 | 20.783 | |
| Cytochrome C | 10 | 5 | | 3 | 24.802 | |
| | | | | | 22.312 | =Average |
| | | | | | 2.175 | =Std dev |
| | | | | | 9.7 | =% CV |
| Cytochrome C | 10 | 5 | X | 1 | 24.526 | |
| Cytochrome C | 10 | 5 | X | 2 | 23.599 | |
| Cytochrome C | 10 | 5 | X | 3 | 23.877 | |
| | | | | | 24.001 | =Average |
| | | | | | 0.476 | =Std dev |
| | | | | | 2.0 | =% CV |

The contents of all references, patents and published patent applications cited throughout this application are incorporated herein by reference.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supersede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A method for quantitation of one or more biomolecules in a sample, the method comprising the steps of:
   (a) providing a sample holder comprising a porous membrane which comprises a hydrophilic region surrounded by a hydrophobic region for sample containment;
   (b) contacting the hydrophilic region of the membrane with a sample volume, wherein the hydrophilic region has a diameter;
   (c) drying the sample volume on the membrane;
   (d) exposing the sample volume on the membrane to an infrared beam having a diameter equal to or larger than the diameter of the hydrophilic region, and comprising a wavelength in the spectral range of 4000-400 cm$^{-1}$ or any portion of the spectral range of 4000-400 cm$^{-1}$, thereby to obtain an infrared absorption spectrum;
   wherein one or more absorption peak areas in the infrared absorption spectrum correlates with the quantity of the one or more biomolecules in the sample.

2. The method of claim 1, wherein the one or more biomolecules is selected from the group consisting of nucleic acids, proteins, lipids, polysaccharides and lipopolysaccharides.

3. The method of claim 2, wherein the lipopolysaccharide is an endotoxin.

4. The method of claim 1, wherein the method does not require a user to generate a calibration curve each time a sample is analyzed for quantitation of the one or more biomolecules.

5. The method of claim 1, wherein sample volume ranges from 0.1-20 µl.

6. The method of claim 5, wherein sample volume is 1 µl or less.

7. The method of claim 1, wherein the porous membrane is contained within a device.

8. The method of claim 7, wherein the device is a sample holder card.

9. The method of claim 8, wherein the sample holder card comprises a porous membrane which comprises an area within which the sample is contained on the membrane.

10. The method of claim 9, wherein the area for sample containment on the membrane comprises a hydrophilic region surrounded by a hydrophobic region.

11. The method of claim 10, wherein the hydrophobic region is created by plasma treatment of a hydrophilic porous membrane.

12. The method of claim 10, wherein the sample is contained within the hydrophilic region.

13. The method of claim 10, wherein the hydrophobic region is created by heat treatment of a hydrophilic porous membrane.

14. The method of claim 1, wherein the sample comprises a biological fluid.

15. The method of claim 14, wherein the biological fluid is selected from the group consisting of blood, plasma, serum and urine.

16. The method of claim 1, wherein the sample comprises cell or tissue lysate.

17. The method of claim 1, wherein the sample is a crude sample.

18. The method of claim 1, wherein the porous membrane is an ultrafiltration membrane.

19. The method of claim 1, wherein the porous membrane is a microporous membrane.

20. The method of claim 1, wherein the porous membrane comprises a polymeric material selected from the group consisting of PVDF (Polyvinylidene fluoride), polytetrofluoroethylene, hydrophilic polytetrofluoroethylene, polyethylene and polypropylene.

21. A sample holder card for use in the method of claim 1, wherein the sample holder card comprises a porous membrane which comprises a hydrophilic region surrounded by a hydrophobic region, wherein the sample is contained within the boundaries of the hydrophilic region.

22. The sample holder card of claim 1, wherein the diameter of the hydrophilic region ranges from 2.0 mm through 10 mm.

23. The sample holder card of claim 1, wherein the diameter of the hydrophilic region ranges from 3.0 mm through 6 mm.

24. A method for quantitation of one or more biomolecules in a sample, the method comprising the steps of:
   (a) providing a sample holder card comprising a porous membrane which comprises a hydrophilic region surrounded by a hydrophobic region for sample containment;
   (b) contacting the hydrophilic region of the membrane with a sample volume;
   (c) drying the sample volume on the membrane;
   (d) detecting the presence of water on the membrane using infrared absorbance and repeating step (c), if necessary, until no water is detected; and (e) exposing the sample volume on the membrane to an infrared beam comprising a wavelength in the spectral range of 4000-400 cm$^{-1}$ or any portion of the spectral range, thereby to obtain an infrared, absorption spectrum;

wherein one or more absorption peak areas in the infrared absorption spectrum correlates with the quantity of the one or more biomolecules in the sample.

\* \* \* \* \*